United States Patent
Rokugawa

[11] Patent Number: 6,110,338
[45] Date of Patent: Aug. 29, 2000

[54] ION SELECTIVE ELECTRODE APPARATUS AND METHOD OF PRODUCING ION SELECTIVE ELECTRODE APPARATUS

[75] Inventor: Kyuji Rokugawa, Tochigi-ken, Japan

[73] Assignee: Kabushiki Kaisha Toshiba, Kawasaki, Japan

[21] Appl. No.: 09/290,546

[22] Filed: Apr. 12, 1999

[30] Foreign Application Priority Data

Apr. 14, 1998 [JP] Japan ................................. 10-101639

[51] Int. Cl.[7] ................................................ G01N 27/26
[52] U.S. Cl. ............................ 204/418; 204/416; 29/825
[58] Field of Search .................................... 204/409, 416, 204/418, 419; 264/41, 45.1; 29/825

[56] References Cited

U.S. PATENT DOCUMENTS 4,758,325  7/1988  Kanno et al. ........................... 204/411
4,935,117  6/1990  Uematsu et al. ....................... 204/411

*Primary Examiner*—T. Tung
*Assistant Examiner*—Alex Noguerola
*Attorney, Agent, or Firm*—Oblon, Spivak, McClelland, Maier & Neustadt, P.C.

[57] ABSTRACT

An ion selective electrode of flowthrough type is used for electrochemical measurement of ion species contained in a biological fluid by the electrode method. In the electrode method, the reaction of an ion and a sensing substance contained in an ion-sensing membrane is electrochemically detected.

plurality of holes are made on a part of the wall of a path for letting the biological fluid flow therethrough. An ion-sensing membrane is formed in the plurality of holes such that each membrane includes a different sensitive ion from the other and the inner surface of the path is kept smooth.

10 Claims, 6 Drawing Sheets

ION SELECTIVE ELECTRODE APPARATUS AND METHOD OF PRODUCING ION SELECTIVE ELECTRODE APPARATUS

BACKGROUND OF THE INVENTION

1. Field of the Invention

The present invention relates to an ion selective electrode of the flowthrough type for use in electrochemical measurement of ion species contained in a biological fluid.

2. Description of the Related Art

There are colorimetric method, flame method, atomic absorption method, coulometric-titration method, and electrode method, used as a measuring method of the electrolyte concentration in samples, such as a blood serum, plasma, and urine. Of these methods, the electrode method has come to be used broadly in recent sears.

Especially, the electrode method is mainly used for concentration measurement of electrolytes such as sodium ion, potassium ion, and chlorine ion, in a clinical inspection field.

The electrode method is a method of electrochemically detecting the reaction of an ion and a sensing substance using an ion-sensing membrane which confine the sensing material sensitive to an ion to be detected. A common method of detecting the electric signal from the sensing membrane is a detection with an Ag/AgCl electrode which is an internal electrode through an electrolyte solution. The method of producing the ion selective electrode used for the electrode method is that the ion-sensing membrane is beforehand made by methods such as casting and then a fragment of the membrane is stuck on an electrode main part. Moreover, when measuring electrolyte concentration in a sample in a clinical inspection, usually two or more ions, such as sodium, potassium, and chlorine, are simultaneously measured. For this reason, the ion selective electrode used in order to measure these ions is used as a complex electrode by combination, for example, unifying or glueing several ion-selective electrodes using packings, such as an O ring.

Since an adhesion area for sticking the ion-sensing membrane is needed for an electrode main part according to the above-mentioned manufacturing method, in order to stick the ion-sensing membrane firmly, an electrode main part had to be large. Adhesion would be difficult if an adhesion side is small. Therefore, there is a limit in miniaturization of an electrode main part in such a method.

On the other hand, a CWE system (which an ion-sensing membrane is) stuck on an Ag/AgCl electrode is also put to practical use. According to this method, since an electrolyte solution is not necessary, it is possible to miniaturize an electrode main part. However, the ion-sensing membrane needs to be formed directly the Ag/AgCl electrode surface by applying material which forms the ion-sensing membrane. In this case, the surface of the ion-sensing membrane is uneven, therefore even if the surface of an ion-sensing membrane is washed with calibration liquid after measurement in this case, a sample tends to remain on the surface of the ion-sensing membrane.

Furthermore, according to the method of combining two or more ion selective electrodes, the path in an electrode through which a sample flows becomes long. Moreover, since the surface the junction side of the path in each electrode is not smooth and continuous, the sample often remains in the portion and an exact measurement result cannot be obtained.

SUMMARY OF THE INVENTION

It is an object of the present invention to provide an ion selective electrode and method of producing the ion selective electrode, wherein the ion selective electrode is small, is able to measure two or more ions in a sample simultaneously, and has few remains of a sample after washing.

To accomplish the above object, an ion selective electrode apparatus according to the present invention comprises a holding portion having a plurality of tanks for containing an electrolyte solution and a path penetrating through a plurality of the tanks for letting a sample flow therethrough, an ion-sensing membrane formed in each of the tanks to enclose at least a portion of the path within the tank for contacting the ion-sensing membrane with an electrolyte solution when the sample flows in the path, the ion-sensing membrane being manufactured by a method comprising the step of making a plurality of holes on the holding portion therethrough to the path; inserting a pin all over the path; filling each of the plurality of holes with a sensing membrane solution having substantially the same ingredient as the holding portion and including a different sensitive ion from the other solution; drying the sensing membrane solutions removing the pin from the path, and an internal electrode dipped in each of the electrolyte solution.

Furthermore, to accomplish the above object, a method of producing an ion selective electrode apparatus according to the present invention comprises the step of preparing a holding portion, having a tank to store an electrolyte solution in the lover part, and that the upper part is open; making a path which penetrates the holding portion; making a plurality holes on the holding portion therethrough to the path; inserting a pin all over the path; filling each of the plurality of holes with a sensing membrane solution having substantially the same ingredient as the holding portion and including a different sensitive ion from the other solution; drying the sensing membrane solution; removing the pin from the path; closing the upper part of the holding portion with a lid which has a pouring hole; and pouring a electrolyte solution from the pouring hole into the holding portion.

According to the present invention, by forming directly an ion sensing membrane on the path which penetrates through holding portion which contains an electrolyte solution using a sensing solution to two or more ions which differ, a miniaturization of an electrode main part is enable, and two or more ions in a sample can be measured simultaneously, and the sample remainder after washing also be made few.

DETAILED DESCRIPTION OF THE PREFERRED EMBODIMENTS

An embodiment of the present invention will be described, with reference to the accompanying drawings.

Figure 1:
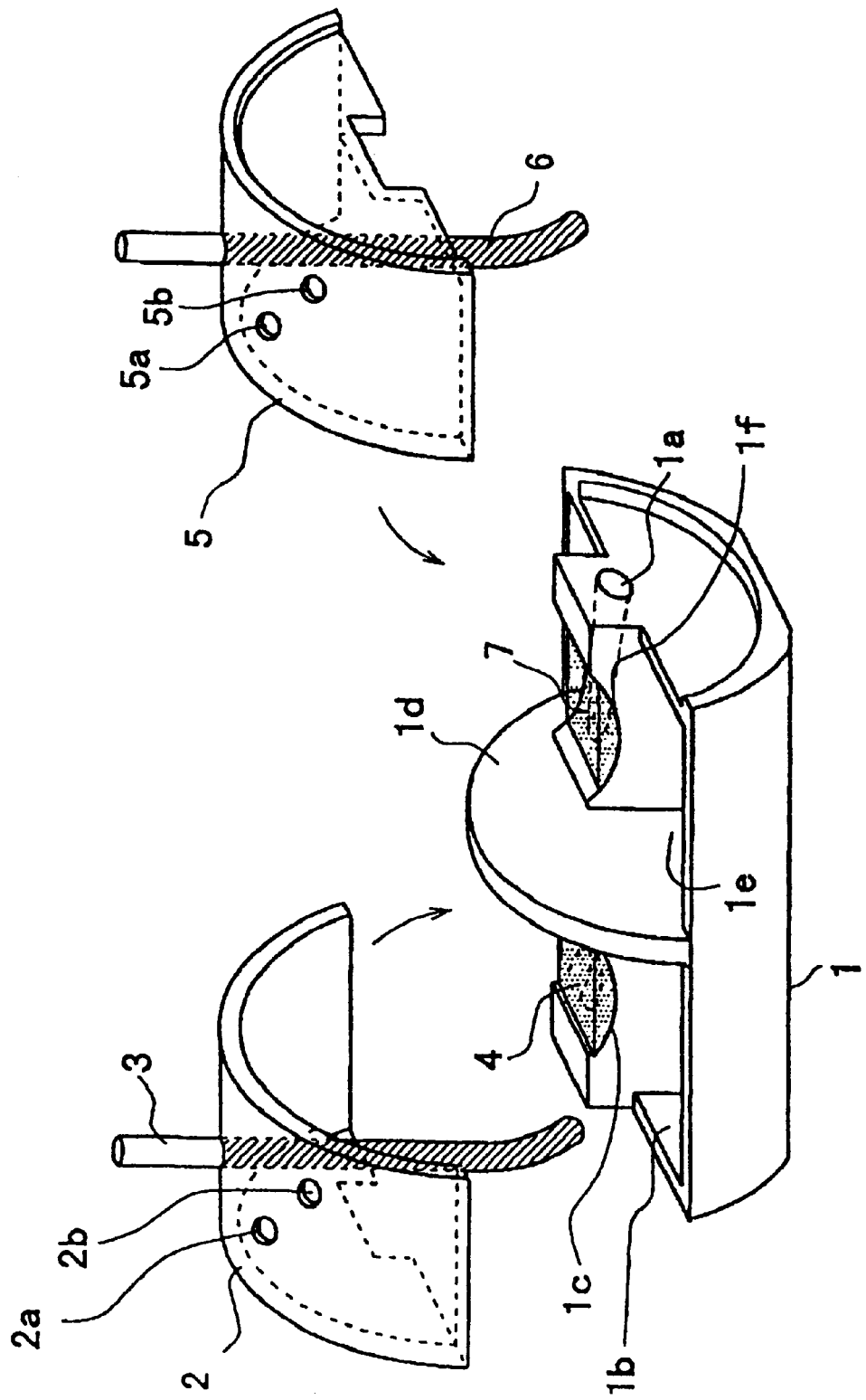
FIG. 1 is a perspective view showing the structure of the ion selectivity electrode of this invention.

FIG. 1 is an exploded perspective view showing the structure of the ion selective electrode according to all embodiment of the present invention. In the figure, an example in which two ion detection electrodes are combined is shown. A holding portion 1 has a half-cylindrical shape and two hollow portions each forming a part of an internal solution tank 1b, 1e. At the center of each hollow portion, a projection portion is provided along the center axis of the half-cylinder. A path 1a penetrates through the projecting portions along the center axis of the half-cylinder. A sensing membrane 4 (K-membrane) and a sensing membrane 7 (Na-membrane) are formed in membrane holes 1c and 1f, respectively each of which is provided on the projecting portion and connected to the path. An electrode main part with a cylindrical shape is constituted by closing the hollow portions of the holding portion 1 with lids 2 and 5 of half-cylinder type. The electrode main part has two cells each of the cells (1 unit electrode) is separated by a wall 1d, and includes an internal solution tank 1b and 1e. The electrode main part is mainly polyvinyl chloride (PVC). An electrolyte solution is held in each of the tanks 1b, 1e of the electrode main part. Ag/AgCl electrodes 3 and 6 are used as internal electrodes and penetrate through and are fixed to the lids 2 and 5, respectively, and are dipped in the electrolyte solution. Moreover, air extraction holes 2a and 5a for extracting air and pouring holes 2b and 5b for pouring in the electrolyte solution are formed in the lids 2 and 5, respectively.

Figure 2:
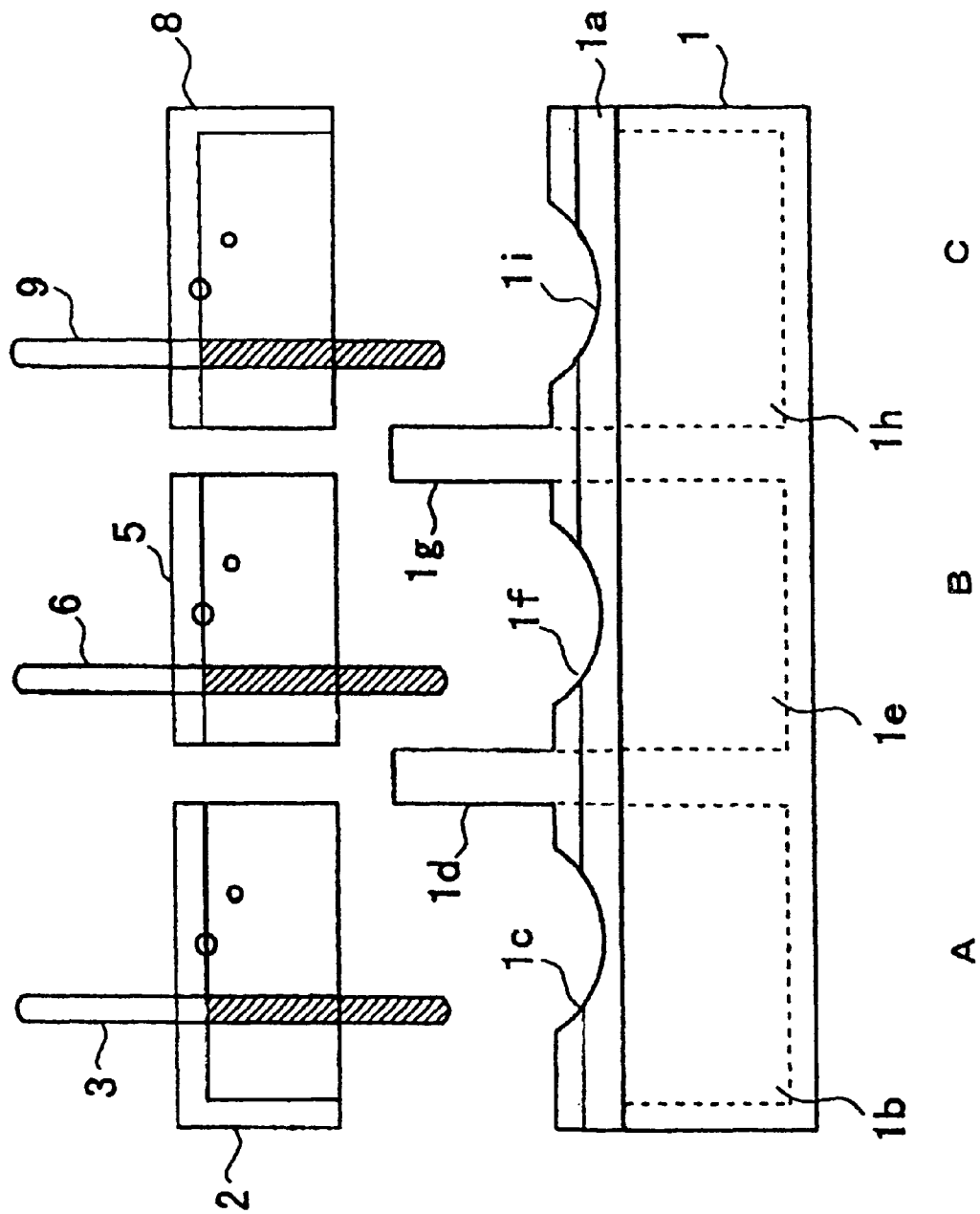
FIG. 2 is a cross-sectional view showing the structure of the ion selectivity electrode of this invention.

FIG. 2 is a cross-sectional view showing the structure of the ion selective electrode of the present invention. The cells A, B, and C for measuring different ions are united in the direction of an axis of the electrode main part. The inside of the electrode main part is separated by walls 1d and 1g.

Figure 3:
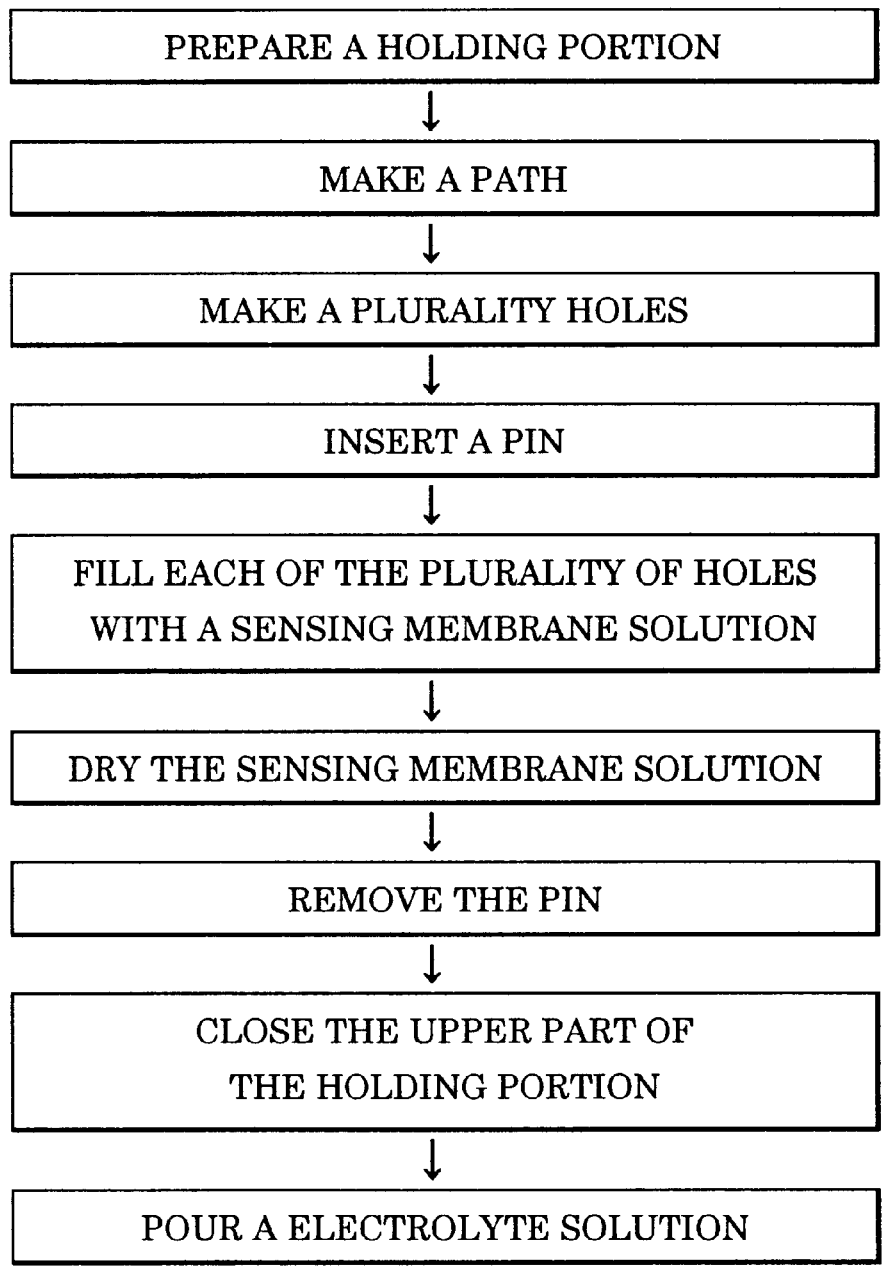
FIG. 3 shows a flowchart representing an outline of a method of producing the ion selective electrode apparatus of the first embodiment of this invention.

FIG. 3 shows the flowchart representing an outline of the method of producing the ion selective electrode apparatus of this invention.

A metal pin, such as a pin of the stainless-steel (SUS) which fits the inner diameter of the path 1a, is inserted in the path 1a of the electrode main part which is beforehand made from PVC. Although a SUS pin is used in this embodiment, the material of the pin can be anything as long as it does not react with ion sensing substances.

After inserting the SUS pin, each of the membrane holes 1c and 1f, which beforehand are prepared in the path 1a, is filled with a sensing membrane solution. The sensing membrane solutions in the holes do not leak into the path since the pin is inserted in the path. The solution is made from PVC dissolved in organic solvent (for example, tetrahydrofuran) to which an ion sensing substance, a plasticizer, etc. is added. Several different types of solutions are made with several ion sensing substances to detect several ions, such as $Na^+$ and $K^+$. Each of the sensing membrane solution is applied in the hole several times using a dispenser, etc. to form a uniform and film sensing membrane. The thickness of the membrane is determined by the amount of the solution applied at a time and the number of applications.

Then, the solution is dried in a dry air flow and the SUS pin is removed from the path. Due to the pin fitted to the inner wall of the path, a membrane facing the path with a smooth and continuous boundary is formed.

Figure 4:
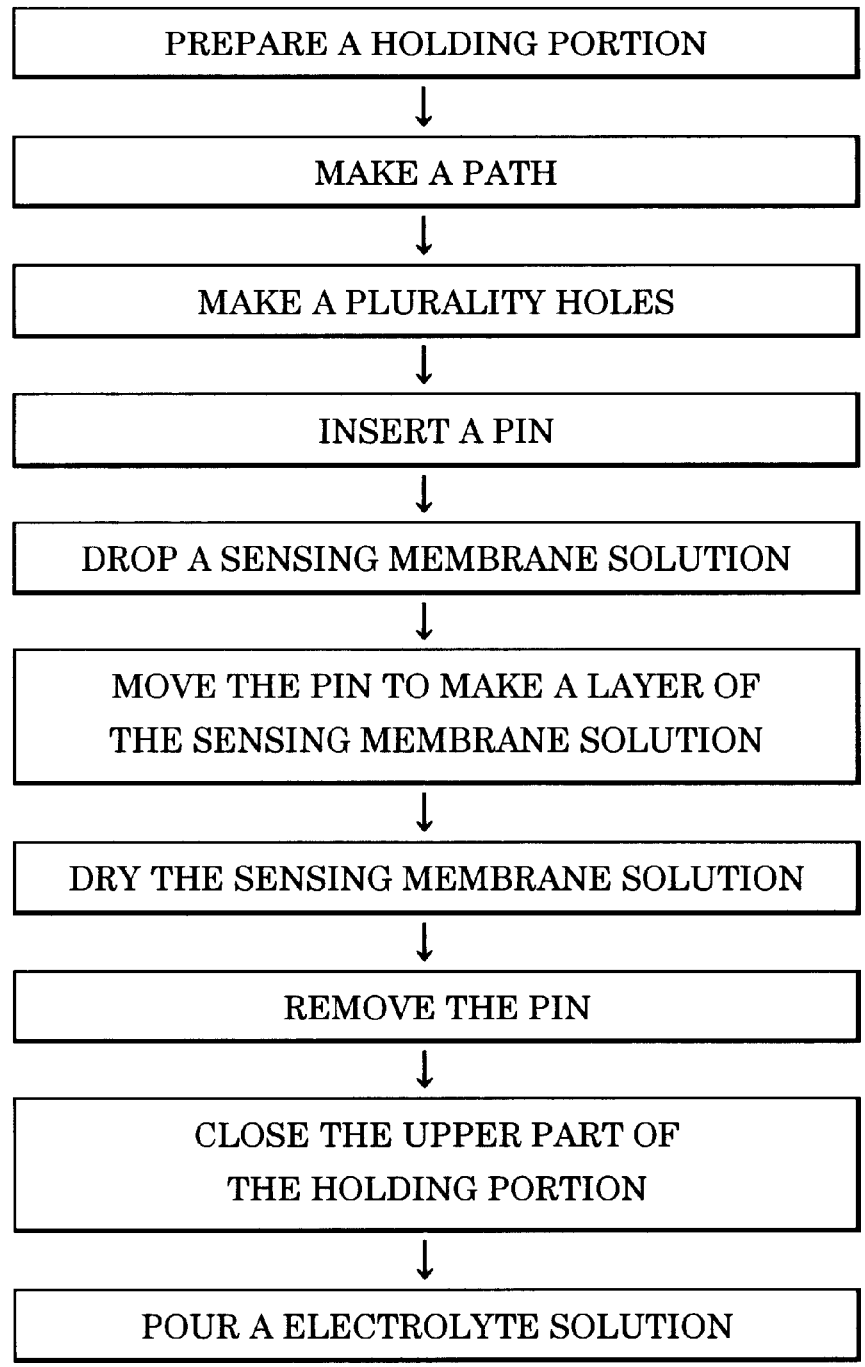
FIG. 4 shows a flowchart representing an outline of a method of producing the ion selective electrode apparatus of the second embodiment of this invention.

In addition to the above, a sensing membrane may be made by the method that after dripping 1 or several drops of the sensing solution in the sensing membrane hole, the SUS pin, which is inserted, may be moved, for example, rotated about its axis (see FIG. 4). The movement produces a layer of the sensing material on the inner surface of the path. Due to the pin fitted to the path, the layer can be thin enough such that the inner surface of the path is substantially smooth and continuous. The layer makes a large surface area of the sensing material, which improves the sensitivity.

Next, the Ag/AgCl electrodes 3 and 6, which are coated with silver chloride on the surfaces by electrolitic deposition, are penetrated and fixed in the lids 2 and 5, respectively. The lids 2 and 5 are glued on the holding portion 1 in which the sensing membranes 4 (K membrane) and 7 (Na membrane) are formed, using adhesives. Then, electrolyte solution is poured into internal solution tanks 1b and 1e from pouring holes 2b and 5b prepared in the lids 2 and 5. The air in the internal solution tanks 1b and 1e are extracted from air extraction holes 2a and 5a as the tanks are filled with the electrolyte solution. After pouring the electrolyte solution, the pouring holes 2b and 5b and the extraction holes 2a and 5a ale closed by adhesive or the like. This completes the process of manufacturing an ion selective electrode of the invention.

Figure 5:
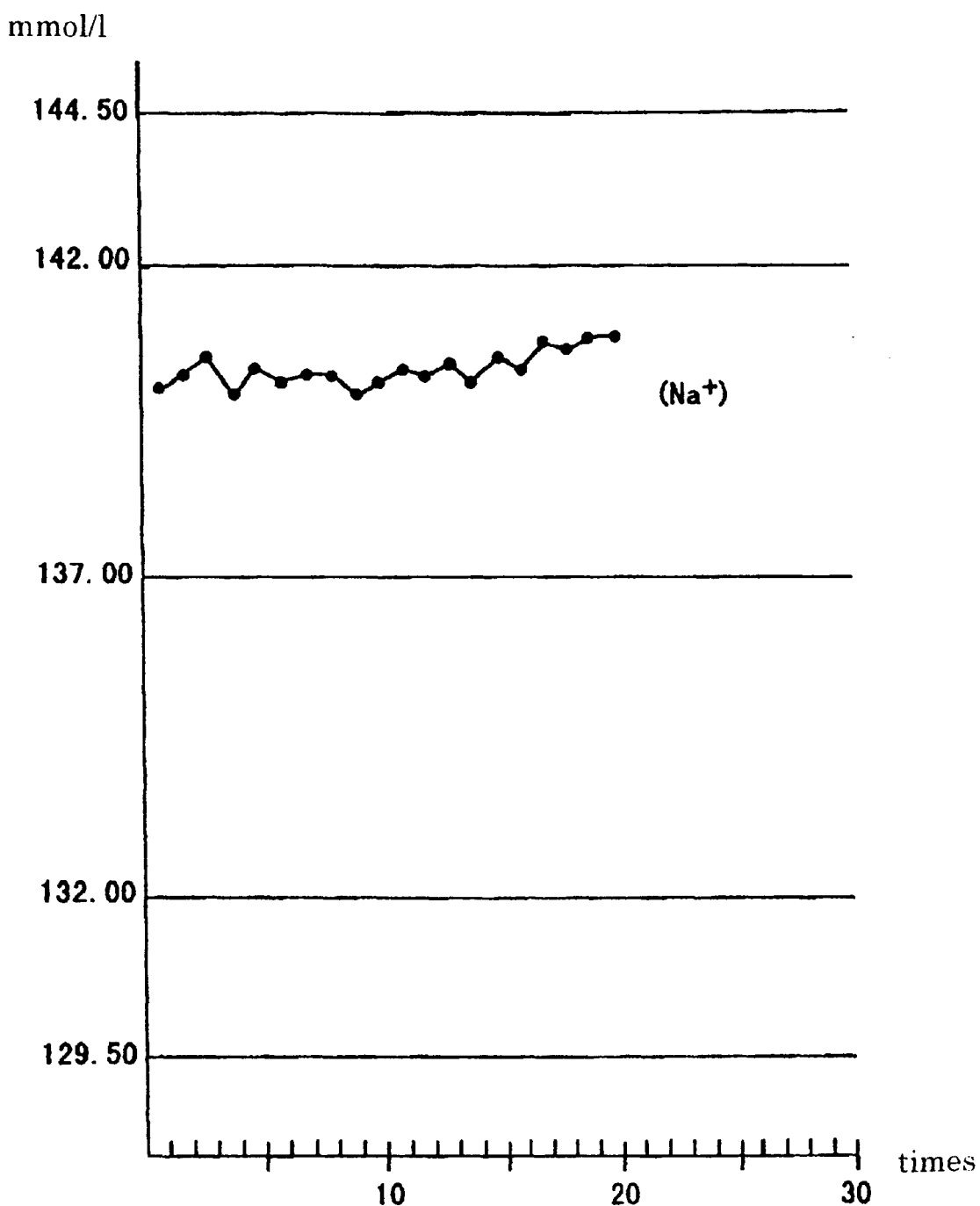
FIG. 5 shows the result of a measurement of the sodium ion using the ion selectivity electrode of this invention.
Figure 6:
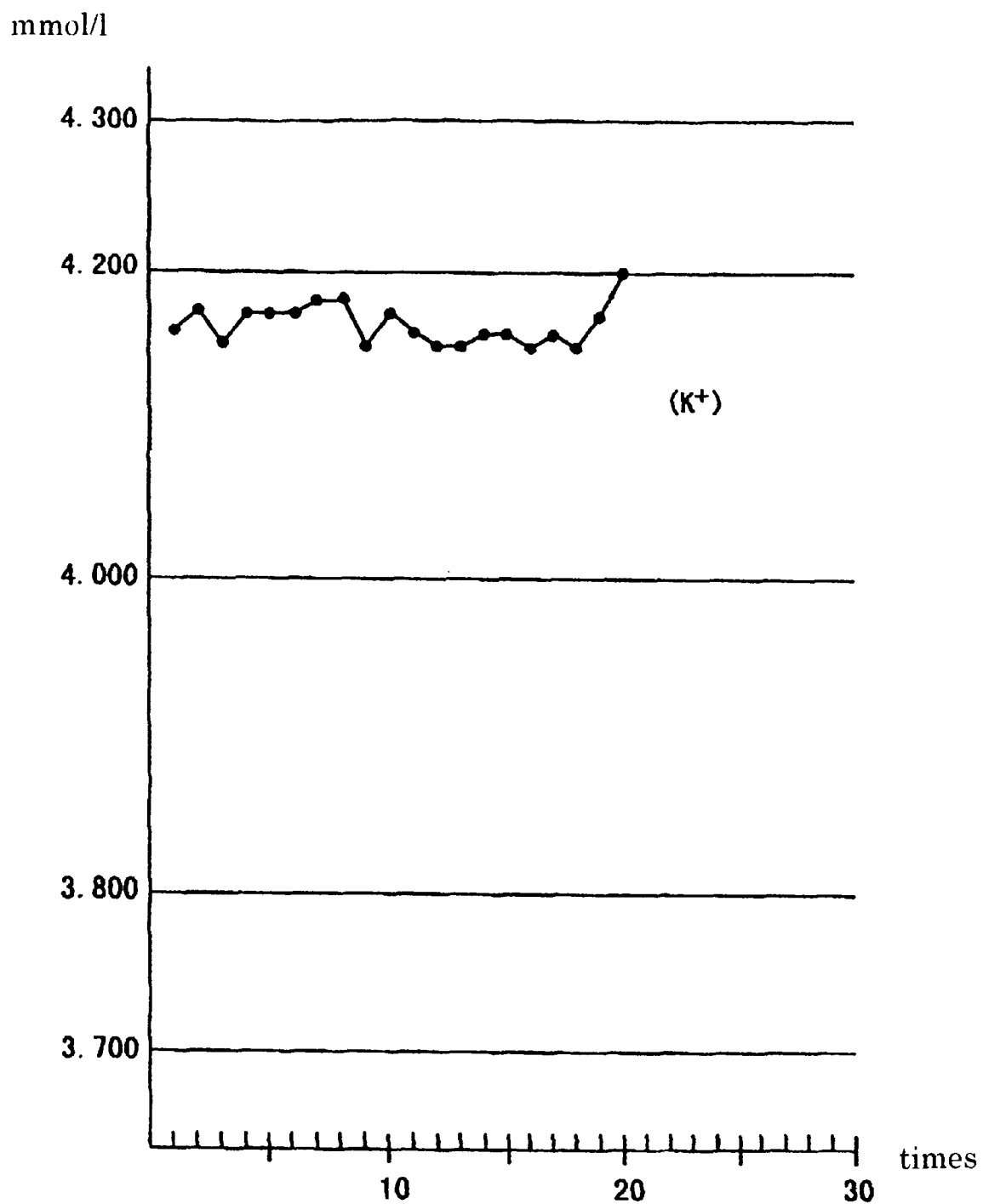
FIG. 6 shows the result of a measurement of the potassium ion using the ion selectivity electrode of this invention.

The ion selectivity electrodes, assembled as mentioned above, are tested repeatedly and the results are shown in FIG. 5 and FIG. 6.

FIG. 5 shows the result of measurements on sodium ion performed 20 times. This result shows that a maximum value is 140.9 mmol/l, a minimum value is 139.9 mmol/l, and the range between the maximum and minimum values is 1.0 mmol/l. In the case of sodium ion, if this range is 2.0 mmol/l or less, it can be considered that the measurement result is stable. Therefore, the measurement result on sodium ion shows that the ion selective electrode of this invention can be considered to be stable enough.

FIG.6 shows the result of measurements on sodium ion performed 20 times. This result shows that a maximum value is 4.20 mmol/l, a minimum value is 4.15 mmol/l, and the range between the maximum and minimum values is 0.05 mmol/l. In the case of sodium ion, if this range is 0.2 or less, it can be considered that the measurement result is stable. Therefore, the measurement result on sodium ion shows that the ion selective electrode of the present invention can be considered to be stable enough.

The following Table 1 shows the results of evaluation of ion-selective electrode units according to the present invention. Two types of multi-cell electrode units (as shown in FIG. 2) are used in the evaluation. One has a Na-membrane in cell A and a K-membrane in cell B, and the other has a K-membrane in cell A and a Na-membrane in cell B:

TABLE 1

| Electrode | membrane potential (mV) | | sensitivity (%) | | reproducibility R | |
|---|---|---|---|---|---|---|
| | Na | K | Na | K | Na | K |
| A | 229.9 | 236.5 | 90.3 | 94.5 | 1.0 | 0.05 |
| B | 216.7 | 226.1 | 93.9 | 98.6 | 1.2 | 0.09 |

In the evaluation especially membrane potential, sensitivity, and reproducibility (same as "range" as above-mentioned). According to this result, With respect to membrane potential, it is almost the same level as the conventional ion selectivity electrode, with respect to sensitivity, since it can be considered to be sufficient for practical use if it generally is 85% or more, it can be considered to be quite good from this result. Moreover, with respect to reproducibility, in the case of sodium ion, if the result is 2.0 mmol/l or less, it can be considered to be stable and, in the case of potassium ion, if the result is 0.2 mmol/l or less, it can he considered to be stable. Therefore, it can be considered that measurement results both on sodium ion and potassium ion are stable enough. As explained above, an ion selective electrode unit can be made to include two or more cells separated by a wall, while conventional cells had to be made independently. These cells correspond to conventional ion selectivity electrode unit. Thus, by making in the unified form, the distance between cells can be minimized and the path through which a sample flows in the electrode unit can be shortened. Therefore, the quantity of a required sample for the measurement can be reduced. Furthermore, since the packing or the adhesives for combining electrode units are unnecessary and excess membrane material does not exist in the path, the inner surface of the path can be kept smooth and continuous, and no sample remains in the path after washing.

As mentioned above, according to the present invention, since the structure includes two or more cells, one, two or more kinds of ions in a sample can be simultaneously measured by a small ion selective electrode unit with a short path, and measurement of ion concentration can be efficiently performed even if the quantity of a sample for measurement is small. Moreover, the uniform and stable ion-sensing membrane with a sufficient ion detection performance can be formed, securing a smooth path.

What is claimed is:

1. A method of making an apparatus for electrochemical measurement of ion concentration in a sample solution, comprising the steps of:

preparing a holding portion, wherein said holding portion includes a tank having an upper part and a lower part, said lower part being for storing an electrolyte solution and said upper part being open;

making a path, wherein said path penetrates said holding portion;

making a plurality of holes in said holding portion, wherein said plurality of holes penetrate through said holding portion to said path;

inserting a pin in said path;

filling each hole of said plurality of holes with a sensing membrane solution, wherein said sensing membrane solution substantially dissolves a same ingredient as said holding portion and said sensing membrane solution is sensitive to a different ion for each hole of said plurality of hole;

drying said sensing membrane solution;

removing said pin from said path;

closing said upper part of said holding portion with a lid, wherein said lid has a pouring hole therethrough; and pouring an electrolyte solution through said pouring hole of said lid into said holding portion.

2. The method according to claim 1, wherein aid lid has a plurality of internal electrodes.

3. The method according to claim 1, wherein said lid has a plurality of air releasing holes.

4. The method according to claim 3, further comprising partition means for partitioning said holding portion.

5. The method according to claim 1, wherein said pin is made of stainless-steel.

6. A method of making an apparatus for electrochemical measurement of ion concentration in a sample solution, comprising the steps of:

preparing a holding portion, wherein said holding portion has a tank having an upper part and a lower part, said lower part for storing an electrolyte solution therein and said upper part being open;

making a path, wherein said path penetrates said holding portion;

making a plurality of holes in said holding portion, wherein said plurality of holes penetrate through said holding portion to said path;

inserting a pin in said path;

dropping a sensing membrane solution, wherein said sensing membrane solution substantially dissolves a same ingredient as said holding portion and said sensing membrane solution is sensitive to another solution for each hole of said plurality of holes;

moving said pin;

making a layer of said sensing membrane solution along an inside wall of said path;

filling each hole of said plurality of holes with said sensing membrane solution;

drying said sensing membrane solution;

removing said pin from said path;

closing said upper part of said holding portion with a lid, wherein said lid has a pouring hole; and pouring an electrolyte solution through said pouring hole into said holding portion.

7. The method according to claim 6, wherein said pin is made of stainless-steel.

8. The method according to claim 6, wherein said holding portion has a plurality of tanks.

9. The method according to claim 8, wherein each tank of said plurality of takes has a lid and each lid of said lids includes a pouring hole and air releasing holes.

10. The method according to claim 9, wherein said pouring hole and said air releasing holes are each a part of said holding portion separated by a wall.

* * * * *